US006274732B1

(12) United States Patent
Cho et al.

(10) Patent No.: US 6,274,732 B1
(45) Date of Patent: Aug. 14, 2001

(54) PROCESS FOR THE PREPARATION OF 1-[(CYCLOPENT-3-EN-1-YL)-METHYL]-5-ETHYL-6-(3,5-DIMETHYLBENZOYL)-2,4-PYRIMIDINEDIONE

(75) Inventors: Eui-Hwan Cho, Seoul; Sun-Gan Chung, Kyungki-do; Sun-Hwan Lee, Kyungki-do; Ho-Seok Kwon, Kyungki-do; Jae-Eung Lee, Kyungki-do; Dong-Wook Kang, Kyungki-do, all of (KR)

(73) Assignee: Samjin Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 09/472,978

(22) Filed: Dec. 28, 1999

(30) Foreign Application Priority Data

Mar. 10, 1999 (KR) .................................... 99-7892

(51) Int. Cl.⁷ ................................................ C07D 239/54
(52) U.S. Cl. ........................................ 544/312; 544/314
(58) Field of Search ..................................... 544/312, 314

(56) References Cited

U.S. PATENT DOCUMENTS 5,922,727  7/1999  Cho et al. ............................ 514/274

*Primary Examiner*—John M. Ford
(74) *Attorney, Agent, or Firm*—Birch, Stewart, Kolasch & Birch, LLP

(57) ABSTRACT

A process for the preparation of the compound of the formula (I) by reacting a compound of the formula (IV) with a compound of the formula (III).

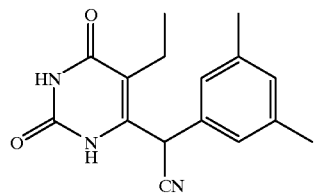

(IV)

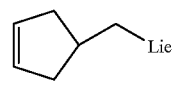

(III)

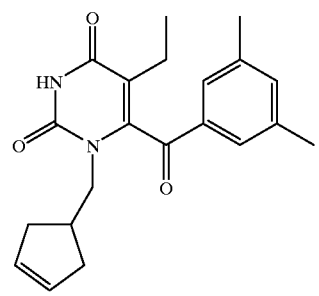

(I)

wherein Lie is a leaving group; and a compound of formula (IV):

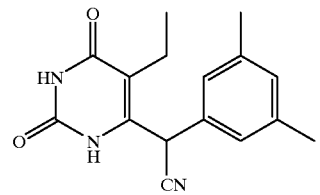

8 Claims, No Drawings

PROCESS FOR THE PREPARATION OF 1-[(CYCLOPENT-3-EN-1-YL)-METHYL]-5-ETHYL-6-(3,5-DIMETHYLBENZOYL)-2,4-PYRIMIDINEDIONE

FIELD OF THE INVENTION

The present invention relates to a process for the preparation of a compound of the general formula (I) and a novel reactant useful for the process.

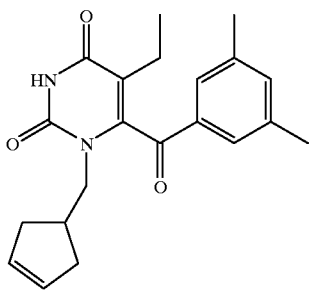

(I)

The inventors have developed the compound of the formula (I) useful as an antivirus agent, especially for the treatment of AIDS (Korean patent application, No. 96-47458; PCT/KR96/00265).

In the above inventions, the compound of the formula (I) may be prepared by reacting a compound of the formula (II) with a compound of the formula (III). The reaction may be represented by the following scheme (1).

Scheme (1)

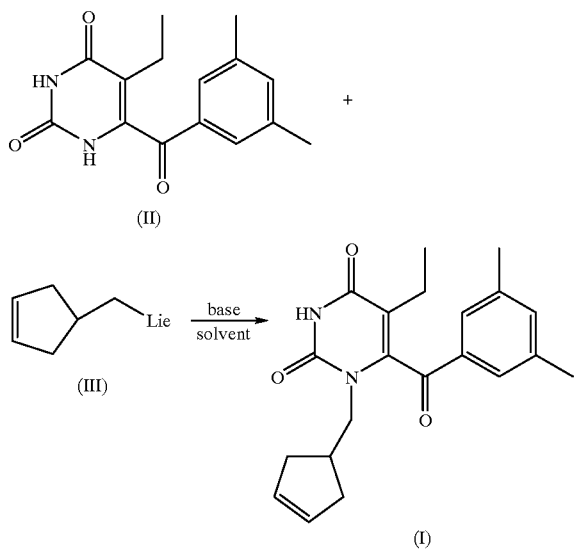

wherein Lie is a leaving group such as halogen atom, alkylsulfonyl, or arylsulfonyl.

The inventors have continued their efforts to improve the process for the preparation of the compound of the formula (I), and now found a novel reactant useful for the process. As the result, a simpler and more economic process for the preparation of the compound can be established by using the novel reactant.

SUMMARY OF THE INVENTION

Accordingly, an object of the invention is to provide a simple and economic process for the preparation of the compound of the formula (I).

Another object of the invention is to provide a new reactant which is useful for the process for the preparation of the compound of the formula (I).

DETAILED DESCRIPTION OF THE INVENTION

The process according to the present invention simplifies the synthesis and increases the yield of the objective compound, and may be represented by the following scheme (2).

Scheme (2)

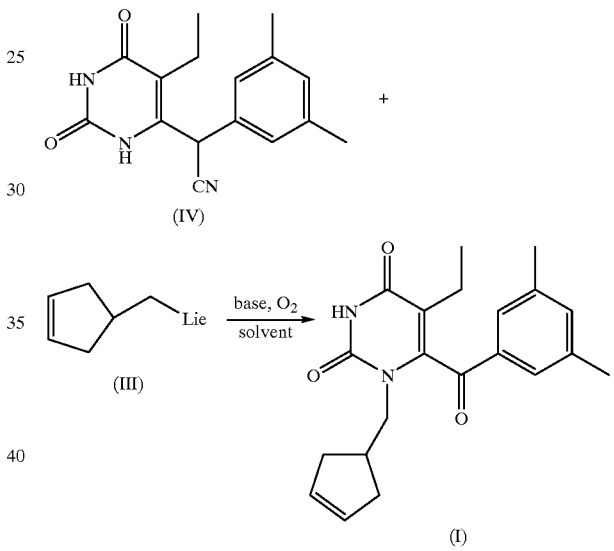

wherein Lie is a leaving group such as halogen atom, alkylsulfonyl, or arylsulfonyl.

The compound of the formula (I) may be prepared by reacting a compound of the formula (IV) with a compound of the formula (III) in the presence of a base with injection of oxygen.

The bases used in the above reaction may include, for example, sodium bicarbonate, sodium carbonate, potassium carbonate and sodium hydride.

The solvents used in the reaction may include organic polar solvents such as dimethylformamide.

The catalysts such as lithium iodide, sodium iodide and potassium iodide may be used in the reaction.

The reaction may be carried out at the temperature of 10–100° C. for 4–72 hours.

Meanwhile, the new reacting compound of the formula (IV) of the invention may be prepared by the following reaction scheme (3).

Scheme (3)

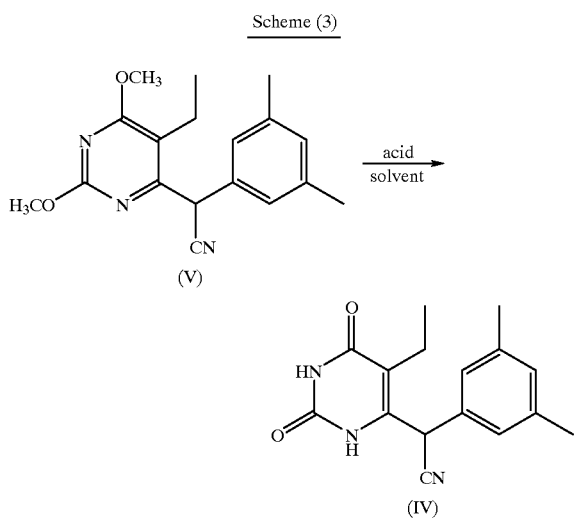

The compound of the formula (IV) may be prepared by hydrolyzing a compound of the formula (V) in the presence of an acid.

The starting material of the formula (V) may be prepared by various known methods.

Acids used in the reaction may include, for example, hydrochloric acid and sulfuric acid.

The reaction may be carried out at the temperature of 25~120° C. for 1–48 hrs.

The examples described below are only for illustrative purpose of the present invention and therefore are not to limit the scope of the invention.

EXAMPLE 1

5-ethyl-6-(α-cyano-3,5-dimethylbenzyl)-2,4-pyrimidinedione (IV)

200 ml of 20% hydrochloric acid was added to 15.0 g of 2,4-dimethoxy-5-ethyl-6-(α-cyano-3,5-dimethylbenzyl)-1,3-pyrimidine (48.2 mmol), and the mixture was refluxed with stirring for 5 hours. The reaction mixture was to be cool, then the resulting white solid was filtered, washed with water and diethylether and dried to obtain 12.1 g of the titled compound as a white solid.

Yield: 88.3%; m.p.: 105~107° C.; $^1$H NMR(500MHz, CDCl$_3$): δ 1.17(3H,t), 2.35(6H,s), 2.52(1H,m), 2.61(1H,m), 5.30(1H,s), 6.99(2H,s), 7.07(1H,s), 8.15(1H,s), 9.07(1H,s).

EXAMPLE 2

1-[(cyclopent-3-en-1-yl)methyl]-5-ethyl-6-(3,5-dimethybenzoyl)-2,4-pyrimidinedione (I)

48 mg of 60% sodium hydride (1.20 mmol) was slowly added to 0.28 g of 5-ethyl-6-(α-cyano-3,5-dimethylbenzyl)-2,4-pyrimidinedione (1.0 mmol) dissolved in 10 ml of dimethyl formamide, and the mixture was stirred at room temperature for one hour. Then, 0.32 g of (cyclopent-3-en-1-yl)methyl bromide (2.0 mmol) was added to the resulting mixture and stirred at the temperature of 50~60° C. for 48 hours with injection of oxygen. After cooling, 20 ml of distilled water was added to the resulting product, and extracted with 20 ml of ethyl acetate (2×). The obtained extract was dried with anhydrous magnesium sulfate and concentrated under the reduced pressure. Then, the concentrated residue was separated and purified with column chromatography (hexane:ethyl acetate=2:1) to obtain 0.23 g of the titled compound as a white solid.

Yield: 65.6%; m.p.: 216~217° C.; $^1$H NMR(500MHz, CDCl$_3$): δ 0.97(3H,t,J=7.5Hz), 2.02(3H,m), 2.28(3H,m), 2.40(6H,s), 2.63(1H,m), 3.21 (1H,dd,J=6.0,8.0Hz), 3.89 (1H,dd,J=6.5,8.0Hz), 5.57(2H,d,J=20.5Hz), 7.34(1H,s), 7.49(2H,s), 8.77(1H,s).

EXAMPLE 3

1-[(cyclopent-3-en-1-yl)methyl]-5-ethyl-6-(3,5-dimethylbenzoyl)-2,4-pyrimidinedione (I)

480 mg of 60% sodium hydride (12.0 mmol) was slowly added to 2.83 g of 5-ethyl-6-(α-cyano-3,5-dimethylbenzyl)-2,4-pyrimidinedione (10.0 mmol) dissolved in 50 ml of dimethyl formamide, and the mixture was stirred at room temperature for one hour. Then, to the resulting solution, 5.07 g of (cyclopent-3-en-1-yl)methyl para-toluenesulfonate (20.0 mmol) was added and stirred with injecting oxygen at 50~60° C. for 48 hours. After cooling, 200 ml of distilled water was added to the resulting product, and extracted with 200 ml of ethyl acetate (2 ×). The obtained extract was dried with anhydrous magnesium sulfate and concentrated under the reduced pressure. Then, the concentrated residue was separated and purified with column chromatography (hexane:ethyl acetate=2:1) to obtain 2.52 g of the titled compound as a white solid.

Yield(%): 71.6%; m.p: 216~217° C.; $^1$H NMR(500 MHz, CDCl$_3$): Identical with those of the example 2.

USEFULNESS OF THE INVENTION

The present invention provides an improved process for the preparation of the compound of the formula (I), which is useful as an antivirus agent, with features of simple process and increased yield.

What is claimed is:

1. A process for the preparation of the compound of the formula (I) by reacting a compound of the formula (IV) with a compound of the formula (III).

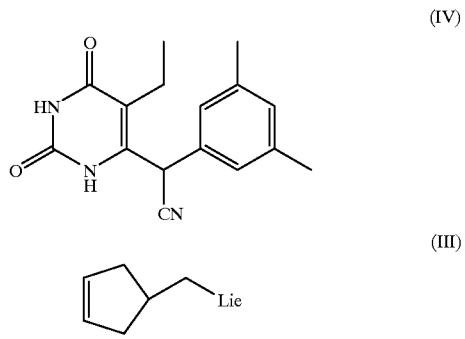

-continued

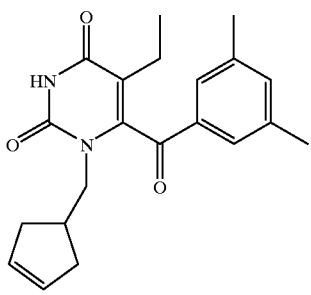
(I)

wherein Lie is a leaving group.

2. The process according to claim 1, characterized in that the compound of the formula (IV) is reacted with the compound of the formula (II) in the presence of a base at the temperature of 10–100° C. for 4–72 hrs with injection of oxygen.

3. A compound of the formula (IV):

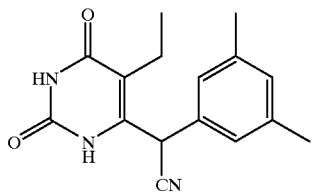

4. The process according to claim 1, wherein Lie is halogen, alkylsulfonyl, or arysulfonyl.

5. The process according to claim 2, wherein the base is sodium bicarbonate, sodium carbonate, potassium carbonate, or sodium hydride.

6. The process according to claim 1, wherein the reaction is performed in the presence of an organic polar solvent.

7. The process according to claim 6, wherein the organic polar solvent is dimethylformamide.

8. The process according to claim 1, wherein the reaction is performed in the presence of a catalyst selected from the group lithium iodide, sodium iodide, and potassium iodide.

* * * * *